United States Patent [19]
Coulter

[11] 3,963,984
[45] June 15, 1976

[54] METHOD AND SYSTEM FOR CLEANING AN APERTURE IN A PARTICLE STUDY DEVICE

[75] Inventor: Wallace H. Coulter, Miami Springs, Fla.

[73] Assignee: Coulter Electronics, Inc., Hialeah, Fla.

[22] Filed: Nov. 4, 1974

[21] Appl. No.: 520,711

[52] U.S. Cl. .................................. 324/71 CP; 134/1
[51] Int. Cl.² ...................... B08B 3/10; G01N 27/02
[58] Field of Search .................... 324/71 CP; 134/1; 137/15; 29/421 E; 72/56

[56] References Cited
UNITED STATES PATENTS

| | | |
|---|---|---|
| 3,232,085 | 2/1966 | Inoue ........................................ 72/56 |
| 3,259,891 | 7/1966 | Coulter et al. ..................... 324/71 CP |
| 3,420,758 | 1/1969 | Scheer ...................................... 134/1 |
| 3,429,743 | 2/1969 | Branson .................................. 134/1 |
| 3,512,384 | 5/1970 | Inoue ...................................... 72/56 |

*Primary Examiner*—John K. Corbin
*Assistant Examiner*—Wm. H. Punter
*Attorney, Agent, or Firm*—Silverman & Cass, Ltd.

[57] ABSTRACT

In both the method and system for clearing the debris from the aperture of a particle study device combinations of pulses of predetermined, waveform amplitude and frequency are developed and coupled through the conductive fluid passing through the particle study device aperture. The pulses cause the fluid in the aperture to vaporize and form a gas. The gas explodes away any debris clogging the aperture as it escapes from the aperture.

12 Claims, 1 Drawing Figure

U.S. Patent June 15, 1976 3,963,984
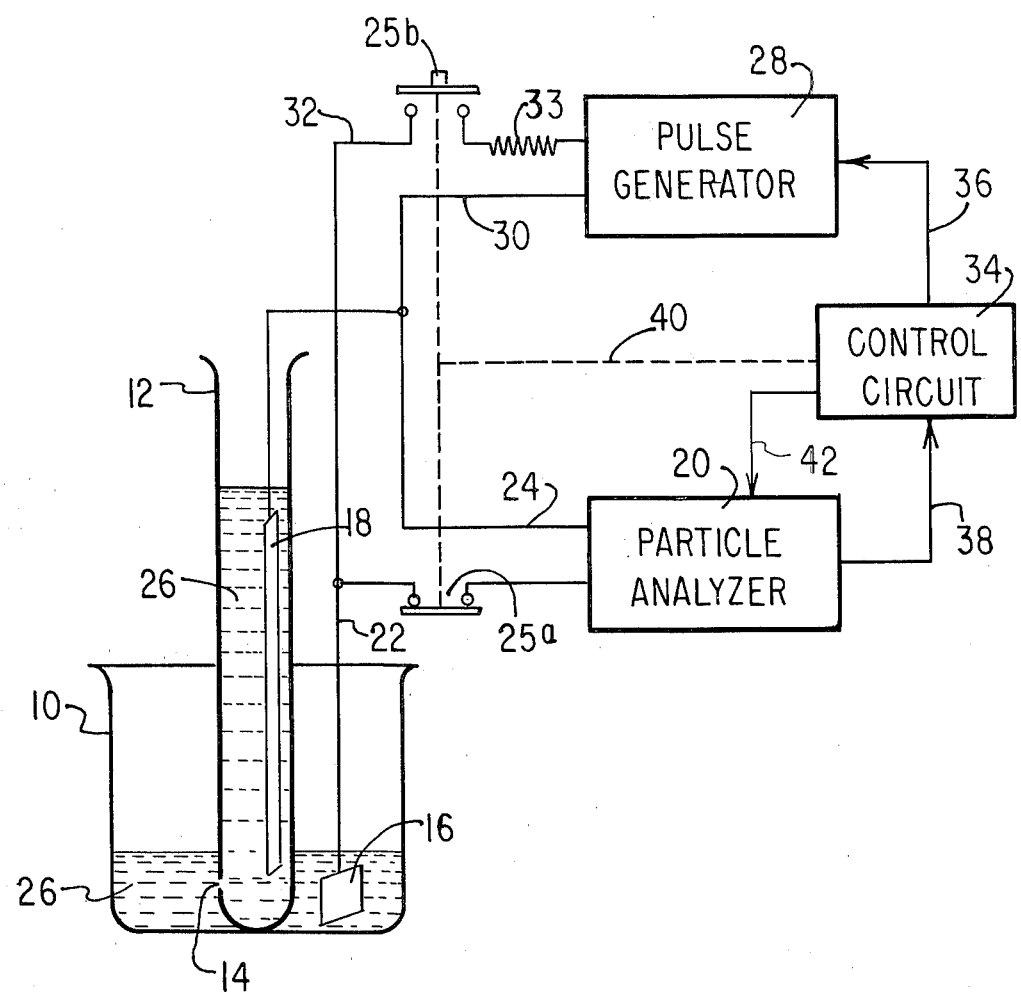

METHOD AND SYSTEM FOR CLEANING AN APERTURE IN A PARTICLE STUDY DEVICE

BACKGROUND OF THE INVENTION

This invention relates generally to particle study devices and is more particularly concerned with means for clearing the aperture employed in such devices.

A particle study device, embodying the Coulter principle such as is shown and described in U.S. Pat. No. 2,656,508, now is well known in the art. Wallace H. Coulter, the patentee of the noted patent, is the same person as the applicant herein. In the Coulter type particle study device, particles of microscopic material are suspended in a fluid whose electrical impedance is different from the electrical impedance of the particles. The fluid is allowed to pass through a microscopic aperture formed in an insulating wall. Electrical excitation in the form of an electric current is applied to the fluid suspension in the aperture, usually by means of electrodes immersed in the fluid suspension on opposite sides of the wall. Due to the dimensions involved, the particles suspended in the fluid flow through the aperture at a very rapid rate and each time a particle passes through the aperture there is a change in the total impedance of the fluid path which is effectively included in the aperture. This change in total impedance coacting with the electrical excitation causes a particle pulse to be developed which is used to count and size the particles passing through the aperture.

In the art of counting and sizing minute particles by used of the Coulter type device, normally the range of particles at its limit is well within the physical diameter of the aperture employed. Experience has shown, however, that even the most specialized suspension of particles will at times produce a blockage, clogging the aperture. Blockages may also be caused by lint, dirt and other debris. Anything which will partially or fully obstruct the aperture will hereinafter be called debris, irrespective of whether it is of the same particulate matter as the particles being studied or whether it is foreign matter.

Circuitry is available for detecting the blockage of the aperture in a Coulter type particle study device. One such debris detection circuit is shown and described in U.S. Pat. No. 3,259,891. Wallace H. Coulter, a co-patentee of this patent is the same person as the applicant herein. In U.S. Pat. No. 3,259,891, debris clearing devices also are shown and described. Certain ones of the devices shown and described require either complex mechanical linkages in order to remove the aperture debris, or the actual removal of the aperture and/or aperture tube. In the former case, the mechanical linkages are cumbersome and somewhat difficult to use. In the latter case removing, cleaning and replacing an aperture tube is a time consuming procedure which is to be avoided. One of the devices shown employs a capacitor charged to a high potential which is discharged via the electrodes creating a very high current flow through the aperture, thereby literally heating the contents of the aperture to explode, driving the obstruction out of the aperture. However, the rate of application of energy from the capacitor is not optimum and when sufficient energy is used to clear a blockage it creates a serious threat of damage to the aperture structure.

SUMMARY OF THE INVENTION

In this application certain terms hereinafter employed will first be defined. A pulse is a change in amplitude for a predetermined time. The amplitude is variable, the waveform is variable, the duration is variable and the polarity is variable. For example, a pulse can be rectangular, sinusoidal or triangular, very short in duration, for example, a nanosecond, or relatively long as for example a second. The pulse polarity can be positive, negative or it can be bipolar.

Repetitive pulses are pulses such as defined above which are repeated at regular fixed or predetermined intervals. All of the repetitive pulses may be alike or a number of them may be different in shape, period, amplitude and polarity.

A pulse train can consist of a grouping of repetitive pulses or a group of pulses which are non-repetitive in character. As defined herein, a pulse train also can include but should not be limited to an RF carrier, amplitude phase or frequency modulated by pulses as defined above, and the envelope formed by a sequence of pulse trains. An RF carrier amplitude modulated by a pulse is sometimes identified as a burst.

A sequence of pulse trains includes a number of pulse trains as defined above in sequence. The sequence can be regular or irregular in period duration or amplitude.

For purposes of this application, repetitive pulses, pulse trains and a sequence of pulse trains will hereinafter be termed combination of pulses.

In practicing this invention, a particle study device of the Coulter type is provided wherein particles to be studied pass through an aperture suspended in a fluid and wherein the aperture clogs with debris. The particle study device includes a system for clearing the debris-clogged aperture. The system includes a first electrode positioned in the fluid suspension on one side of the aperture and a second electrode positioned in the fluid suspension on the other side of the aperture. A pulse generator is coupled to the first and second electrodes and develops a combination of pulses having predetermined characteristics which are coupled to the electrodes. The electrodes in turn couple the pulses through the fluid suspension to the fluid contents of the aperture, which is the principle resistance in the pulse path. Because of this high resistance, the pulses will dissipate primarily in the fluid contents of the aperture, causing the fluid to vaporize and form a gas. The formation of the gas constitutes a microscopic explosion. The force of this explosion is controlled by the characteristics of the combination of pulses and is adjusted to be forceful enough to dislodge the debris without causing damage to the aperture.

The force of this microscopic explosion, being small in order to avoid damage to the aperture, can be repeated rapidly, but at such a repetition rate that the total amount of energy delivered to the vicinity of the aperture in any predetermined period does not destroy the aperture. This repetition rate and the amount of power dissipated in any time period is influenced by the size of the aperture and the resonant frequencies of the various bodies of liquid and mechanical structures associated with the aperture.

The method of generating combinations of pulses and dissipating them in the liquid contents of the aperture in order to vaporize it for the purpose of exploding away debris is also contemplated as being within the scope of this invention.

BRIEF DESCRIPTION OF THE DRAWING

The drawing is a block diagram of a particle study device embodying the system of this invention.

DESCRIPTION OF THE PREFERRED EMBODIMENT

Referring to the drawing, there is shown a beaker 10 and aperture tube 12 positioned inside beaker 10. Both beaker 10 and aperture tube 12 are made of an insulating material such as glass, and are interconnected by means of a fine insulated constriction or aperture 14. An electrode 16 is placed in beaker 10 on one side of aperture 14, and an electrode 18 is placed in aperture tube 12 on the other side of aperture 14. Electrodes 16 and 18 are connected to a particle analyzer 20 of the Coulter type via conductors 22 and 24 respectively. A normally closed switch 25 is in series with conductor 22.

A conductive fluid suspension containing particles to be studied is shown generally at 26 in both aperture tube 12 and beaker 10. In order to induce the flow of suspension 26 from aperture tube 12 to beaker 10, the level of fluid medium 26 in aperture tube 12 is set higher than the level of fluid medium 26 in beaker 10 so that there will be a pressure differential or head tending to cause the fluid suspension 26 to flow from one vessel to the other by way of aperture 14. Although the apparatus is shown without apparatus for setting two different levels of suspension in beaker 10 and aperture tube 12 in order to force flow, it is to be understood that the level differential between the two can be set via use of a manometer-syphon device such as is commonly known in the art. Flow also can be induced via use of a suction or pressure type device.

When current is permitted to flow from particle analyzer 20, it will flow through conductors 22 and 24, electrodes 16 and 18 and fluid medium 26 establishing a $a_k$ current flow and potential in aperture 14. The fluid has an electrical conductivity or impedance which is different from the impedance of the particles. Whenever a particle passes through aperture 14, the total impedance of the contents of the aperture will vary causing a modulation of the current flow and/or potential. This modulation of the current flow and/or electric field creates an electrical change which will be detected by particle analyzer 20 and can be used in order to count and size the particle passing through aperture 14.

In the embodiment shown, electrode 18 also is connected to a pulse generator 28 via conductor 30. Electrode 16 is connected to pulse generator 28 via conductor 32, normally open push button switch 25B and resistor 33. Switches 25A and 25B are shown ganged together and simultaneously operable from a single push button. They can, of course, be automatically operated as noted in a later portion of this application. Pulse generator 28 can develop a combination of pulses having predetermined characteristics such as for example pulse width, repetition rate, and waveform or envelope. It can be variable so that the combination of pulses can be adjusted for any and all of these characteristics within a substantial range. If aperture 14 becomes clogged with debris, pulse generator 28 is so adjusted and set to develop a predetermined combination of pulses. Push button 25B is then operated, coupling the combination of pulses to electrodes 16 and 18. As fluid suspension 26 is conductive, the combination of pulses are coupled from electrode 16 and 18 through fluid suspension 26 to the contents of the aperture 14. Since the total path resistance is concentrated almost entirely in the aperture, the energy in the combination of pulses is dissipated in aperture 14, causing the fluid suspension 26 in aperture 14 rapidly to increase in temperature and vaporize, forming a gas. The gas formed by the vaporization of fluid suspension 26 is under very high pressure, and when it expands, takes up a greater volume than the fluid medium itself, forcing the contents out of aperture 14 at a very rapid rate effectively "exploding" the debris out of aperture 14. The gas formed can escape the fluid suspension in the form of bubbles. As the gas escapes from the aperture area fluid suspension 26 will re-enter the aperture 14 creating a washing action further clearing any debris. Since this same pressure is applied to the walls of the aperture 14, care must be taken that this pressure is not sufficient to crack its walls. Therefore, the manner in which the combination of pulses varies with time must be chosen to provide the maximal acceleration of the fluid contents of the aperture 14 due to the gas expansion while maintaining minimal stress at the aperture walls.

As noted previously, the amount of energy dissipated is limited by the combination of pulses. Consequently it may be desirable or necessary in order to achieve the desired cleaning effect to repeat the combination of pulses many times, Although combination of pulses includes within its definition a sequence of pulse trains, this type of operation, in the form of repetitive combinations of pulses is reiterated here for clarity even though it may be redundant. Again care must be taken to insure that the energy dissipated by a repetitive combustion of pulses does not damage aperture 14.

Pushbutton switches 25a and 25b are ganged together and simultaneously operable in order to protect particle analyzer 20. Operation of pushbutton 25b closes its contacts and opens the contacts of switch 25a, open circuiting the electrical path between particle analyzer 20 and pulse generator 28. This prevents the relatively high voltage pulses, developed by pulse generator 28 for clearing aperture 14, from being coupled to and damaging the circuitry in particle analyzer 20. After the debris clogging aperture 14 has been removed, pushbutton 25b may be released terminating the transmission of pulses. The entire apparatus can then revert to use as a particle study device wherein particle analyzer 20 counts and sizes the particles passing through aperture 14.

The above described equipment requires that a technician or operator operate the particle analyzer, then monitor the operation of the equipment. If a blockage occurs the operator must manually operate pulse generator 28 to clear the debris from aperture 14. Referring again to the drawing, a control circuit 34 is shown coupled to pulse generator 28 via conductor 36 and to particly analyzer 20 via conductor 38. Upon initiation of operation, particle analyzer 20 couples a start signal to control circuit 34 via conductor 38. Control circuit 34 develops a control signal for a predetermined period of time of, for example, 100 milliseconds in response to the start signal and couples the control signal to pulse generator 28 via conductor 36. Pulse generator 28 is operative to develop combinations of pulses for the predetermined period of time in response to the control signal. Switches 25a and 25b which are preferably electronic switches in the automated embodiment are electrically or solenoid operated from control circuit 34 when the control signal is developed, as represented by line 40, allowing the combinations of pulses developed by pulse generator 28 to be coupled to aperture 14 for clearing the aperture. After the aperture has cleared, particle analyzer 20 can proceed to analyze electrical changes generated by the passage of particles through aperture 14.

In one mode of operation, when particle analyzer 20 completes its operational cycle, it couples a stop signal to control circuit 34 via conductor 38. The cycle described above resulting from the start signal will be repeated in response to the stop signal in order to insure that aperture 14 is clear of all debris.

Control circuit 34 provides for the automatic clearing of aperture 14 prior to and/or after operation of particle analyzer 20, thus reducing the need to check the aperture prior to and after particle analysis. Particle analyzer 20 can also include a debris alarm such as is described in U.S. Pat. No. 3,259,891. The debris alarm output can also be coupled to control circuit 34 for initiating operation of the control circuit whenever the aperture clogs.

In another mode of operation, control circuit 34 incorporates a clock and periodically automatically operates switches 25a and 25b to disconnect the particle analyzer 20 from and to connect the pulse generator 28 to electrodes 16 and 18. The clock then initiates operation of pulse generator 28 causing combinations of pulses to be coupled to aperture 14 for clearing the aperture.

It has been found experimentally that frequencies between 5KHz and a 100 KHz are most effective for unclogging aperture 14 when aperture 14 is approximately 100 microns in diameter and the fluid 26 is physiological saline. A very effective combination of pulses within this range and for these conditions appears to be a train of one microsecond rectangular pulses with a repetition rate of 10 KHz and with an applied voltage of approximately 200 volts from the pulse generator 28. Assuming that the protective resistance 33 has a resistance of 15,000 ohms, which is about equal to the resistance between the electrodes 16 and 18 under these conditions, the voltage actually appearing across the aperture will be approximately 100 volts and each combination of pulses will amount to roughly ⅔ of a watt. A sapphire wafer can withstand many cycles of this cleaning procedure without damage.

It should be noted that although there is a possibility of damaging the aperture by application of excessive power, the possibility of damage is substantially lessened as compared to the possibility of damage via discharge of a capacitor. Accordingly, the use of a variable pulse generator provides a means for clearing debris from an aperture while substantially eliminating the problems heretofore present with aperture clearing systems.

It will be apparent to those skilled in the art that pulse generator 28 may be of many different forms, from a simple unidirectional pulse generator to a switched source of high frequency power. The use of alternating polarity "DC" pulses or bursts of high frequency alternating current will sometimes prove useful in avoiding electrode polarization when the aperture diameter is so large that the electrodes cannot be made correspondingly large. The embodiment described is meant to be exemplary and not limiting.

It is believed that the above explained theory of operation regarding vaporization of the fluid is correct; however, it is not intended to be limiting. Due to the very unpredictable resistance of the aperture when plugged and the cooling due to the flow of electrolyte when not completely plugged, the explanation of the action may not be completely accurate. It has been shown experimentally that the desired clearing action is realized by the application of electrical power as described. It is also possible that the heating of the aperture contents at the indicated repetition rates produces an action in the fluid somewhat like ultrasonic cleaning action.

What it is claimed and desired to secure by Letters Patent of the United States is:

1. In a particle study device having an aperture through which particles to be studied pass, which aperture clogs with debris, and wherein the particles are suspended in an electrically conductive fluid which flows through said aperture, an aperture cleaning system including in combination,
    a first electrode positioned in said fluid an on one side of said aperture,
    a second electrode positioned in said fluid and on the second side of the said aperture,
    Pulse generation means for developing combinations of pulses, having a repetition rate approximately in the range of 5 to 100 KHz said electrodes being coupled to said pulse generation means and operative to couple said combinations of pulses through said fluid and said aperture between said first and second electrodes, said fluid in said aperture being responsive to said pulses passing therethrough to remove said debris clogging said aperture.

2. The system of claim 1 further including switch means coupled between said first and second electrodes and said pulse generation means for selectively coupling said pulse generation means to said electrodes.

3. The system of claim 1 wherein said pulse generation means is a pulse generator and said combinations of pulses have a repetition rate of approximately 10 KHz.

4. The system of claim 1 wherein said pulse generation means is a pulse generator.

5. The system of claim 1 further including, control means coupled to said pulse generation means and operative to develop a control signal in response to predetermined conditions, said pulse generation means being operative to develop said combinations of pulses in response to said control signal.

6. The system of claim 1 wherein said electrodes are further selectively coupled to a particle analyzing device and are operative in response to electrical excitation received therefrom and passage of a particle through said aperture to develop a particle pulse.

7. The system of claim 6 wherein said particle analyzing device develops a first signal, and further including, control means coupled to said particle analyzing device and said pulse generation means and operative in response to said first signal to develop a control signal, said pulse generation means being operative to develop said combinations of pulses in response to said control signal.

8. The system of claim 7 wherein said first signal is at least one of a start signal, stop signal and debris alarm signal.

9. The system of claim 1 wherein said fluid in said aperture vaporizes in response to said combinations of pulses passing therethrough said vaporized fluid exploding said debris from said aperture.

10. In a particle study device having an aperture through which particles to be studied pass and which clogs with debris, and wherein the particles are suspended in an electrically conductive fluid which flows through said aperture, a method of clearing the aperture of debris including the steps of:

developing combinations of pulses of predetermined amplitude, frequency, waveform, and repetition and having a repetition rate approximately in the range of 5 to 100 KHz, coupling said pulses through said electrically conductive fluid and said aperture for exploding said debris from said aperture.

11. The method of claim 10 wherein said pulses vaporize the fluid in the aperture and explode said debris from said aperture by allowing said vaporized fluid to escape.

12. The method of claim 10 wherein said step of coupling said combinations of pulses through said fluid and aperture includes selectively coupling said combinations of pulses to said fluid and aperture.

* * * * *